United States Patent
Hasegawa et al.

(10) Patent No.: US 10,751,459 B2
(45) Date of Patent: Aug. 25, 2020

(54) BLOOD PURIFICATION APPARATUS

(71) Applicant: Nikkiso Company Limited, Tokyo (JP)

(72) Inventors: Shinya Hasegawa, Shizuoka (JP);
Tomohiro Furuhashi, Shizuoka (JP);
Satoshi Takeuchi, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 300 days.

(21) Appl. No.: 15/788,040

(22) Filed: Oct. 19, 2017

(65) Prior Publication Data

US 2018/0036470 A1 Feb. 8, 2018

Related U.S. Application Data

(63) Continuation of application No. PCT/JP2016/062533, filed on Apr. 20, 2016.

(30) Foreign Application Priority Data

Apr. 20, 2015 (JP) ................................ 2015-086167

(51) Int. Cl.
*A61M 1/30* (2006.01)
*A61M 1/36* (2006.01)

(52) U.S. Cl.
CPC .............. *A61M 1/301* (2014.02); *A61M 1/30* (2013.01); *A61M 1/306* (2014.02);
(Continued)

(58) Field of Classification Search
CPC .. A61M 1/301; A61M 1/3644; A61M 1/3638; A61M 1/3626; A61M 2205/18;
(Continued)

(56) References Cited

U.S. PATENT DOCUMENTS

| | | | | |
|---|---|---|---|---|
| 4,596,550 A | * | 6/1986 | Troutner | A61M 1/30 128/DIG. 13 |
| 4,776,837 A | * | 10/1988 | Kopp | A61M 1/30 128/DIG. 13 |
| 4,828,543 A | * | 5/1989 | Weiss | A61M 1/16 210/637 |
| 5,034,135 A | | 7/1991 | Fischel | |

(Continued)

FOREIGN PATENT DOCUMENTS

| JP | H05-168704 | 7/1993 |
|---|---|---|
| JP | 2010/004906 | 1/2010 |

OTHER PUBLICATIONS

International Search Report from the Japanese Patent Office for Application No. PCT/JP2016/062533 dated Jul. 12, 2016.
(Continued)

*Primary Examiner* — David C Mellon
(74) *Attorney, Agent, or Firm* — Young Basile Hanlon & MacFarlane, P.C.

(57) ABSTRACT

A blood purification apparatus employing a single-needle double-pump method and being capable of automatically discharging a priming solution that has undergone substitution from a blood circuit during blood removal. A blood purification apparatus includes a blood circuit to which an only puncture needle is connectable, a dialyzer that purifies blood flowing in the blood circuit, a first blood pump, a second blood pump, and a control device that allows the blood of a patient to be extracorporeally circulated through the blood circuit by causing the first blood pump and the second blood pump to alternately undergo normal rotation. During blood removal, the control device operates to substitute a priming solution in the blood circuit with the blood of the patient and to discharge the priming solution having undergone the substitution from the blood circuit by causing the first blood pump to undergo normal rotation and the second blood pump to undergo reverse rotation.

17 Claims, 8 Drawing Sheets

(52) U.S. Cl.
CPC ........ *A61M 1/3639* (2013.01); *A61M 1/3644* (2014.02); *A61M 1/3626* (2013.01); *A61M 1/3638* (2014.02); *A61M 2205/18* (2013.01); *A61M 2205/3306* (2013.01); *A61M 2205/3331* (2013.01); *A61M 2205/3341* (2013.01); *A61M 2205/3365* (2013.01); *A61M 2230/207* (2013.01)

(58) Field of Classification Search
CPC .. A61M 2205/3306; A61M 2205/3331; A61M 2205/3365; A61M 2230/207; A61M 2205/3341; A61M 1/3639; A61M 1/30; A61M 1/3621; A61M 1/3624; A61M 1/3627; A61M 1/3633; A61M 1/3643; A61M 1/3646; A61M 1/3647; A61M 1/3649; A61M 1/365; A61M 1/3653; A61M 1/3663; A61M 1/305; A61M 1/306
See application file for complete search history.

(56) References Cited

U.S. PATENT DOCUMENTS

| | | |
|---|---|---|
| 5,120,303 A | 6/1992 | Hombrouckx |
| 2012/0029409 A1 | 2/2012 | Rada |
| 2013/0261529 A1 | 10/2013 | O'Mahony |

OTHER PUBLICATIONS

Extended European Search Report from the European Patent Office for Application No. PCT/JP2016/062533, dated Nov. 19, 2018.

\* cited by examiner

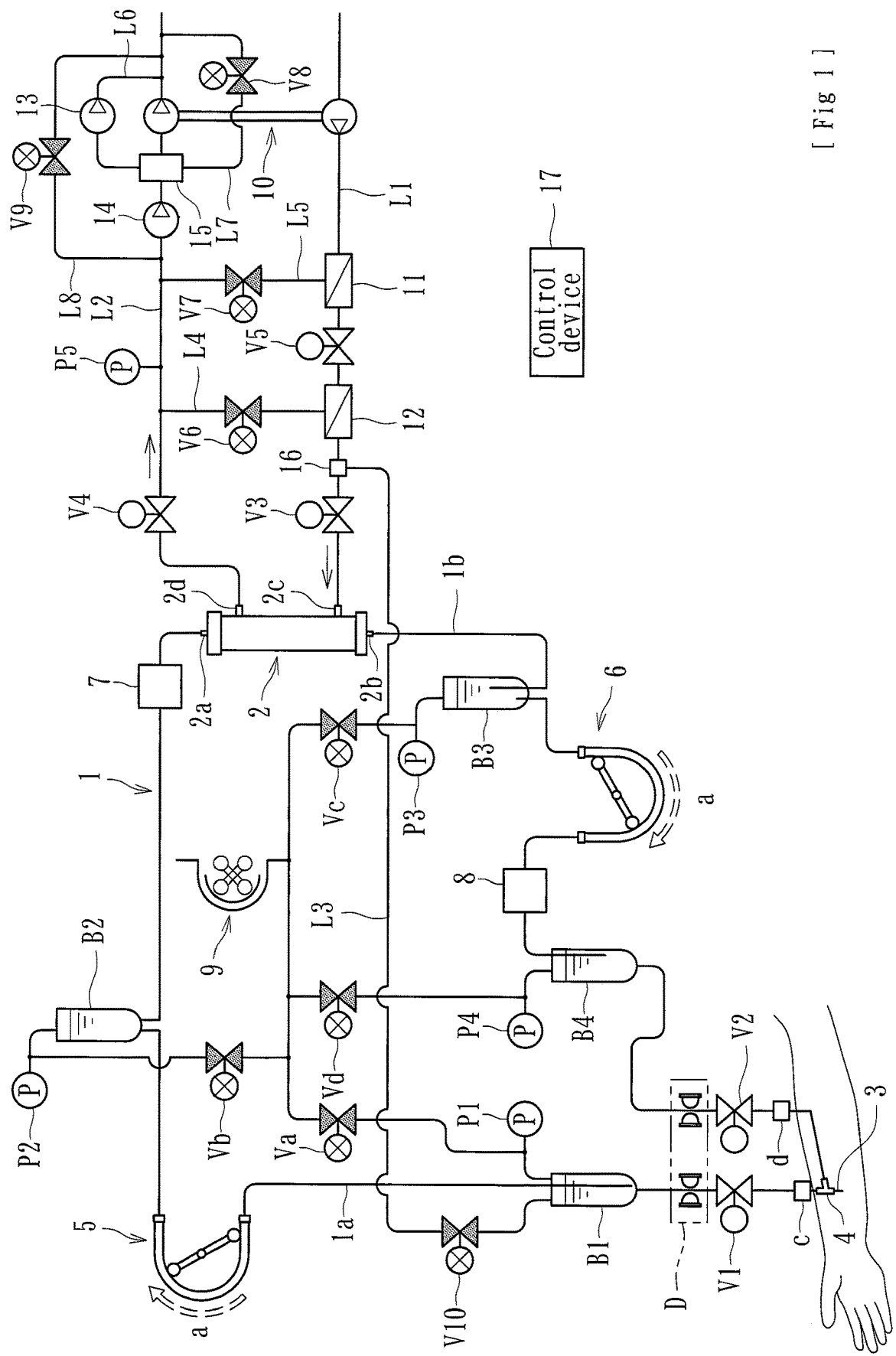
[Fig 1]

[Fig 2]
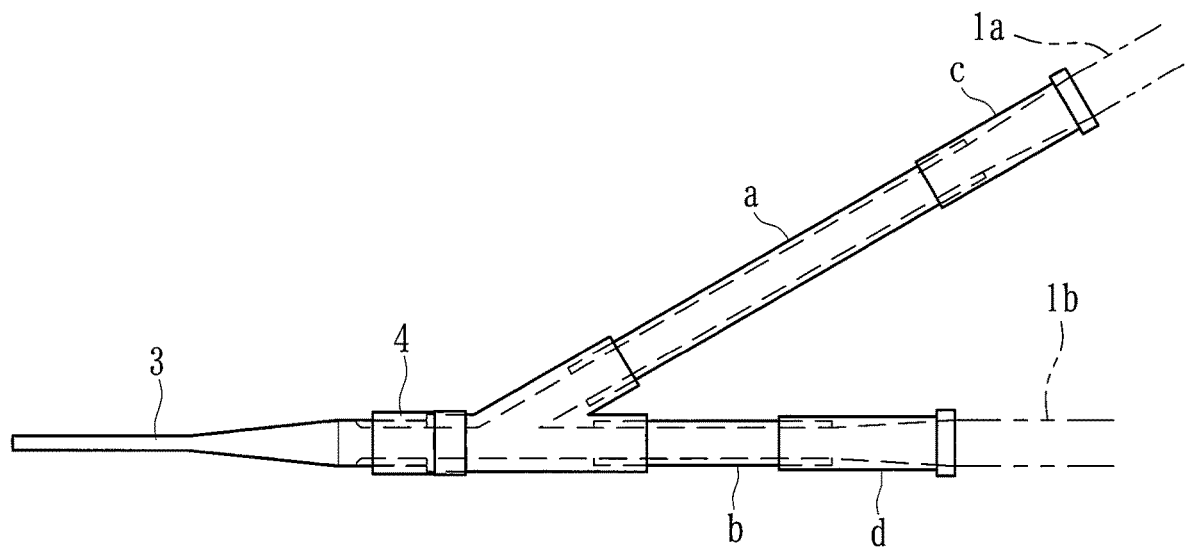
[Fig 3]
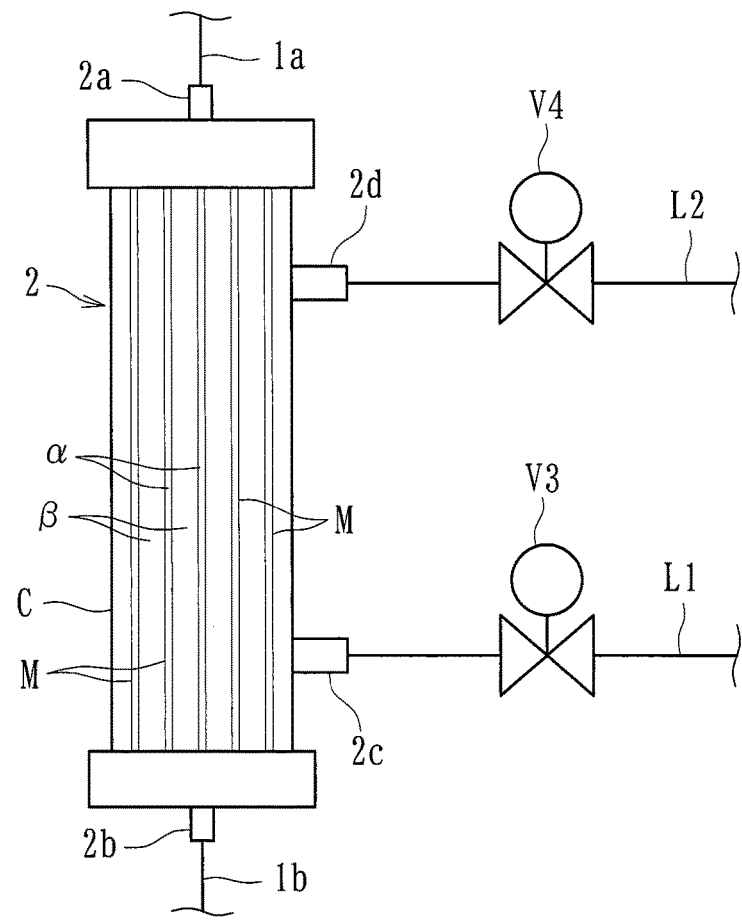

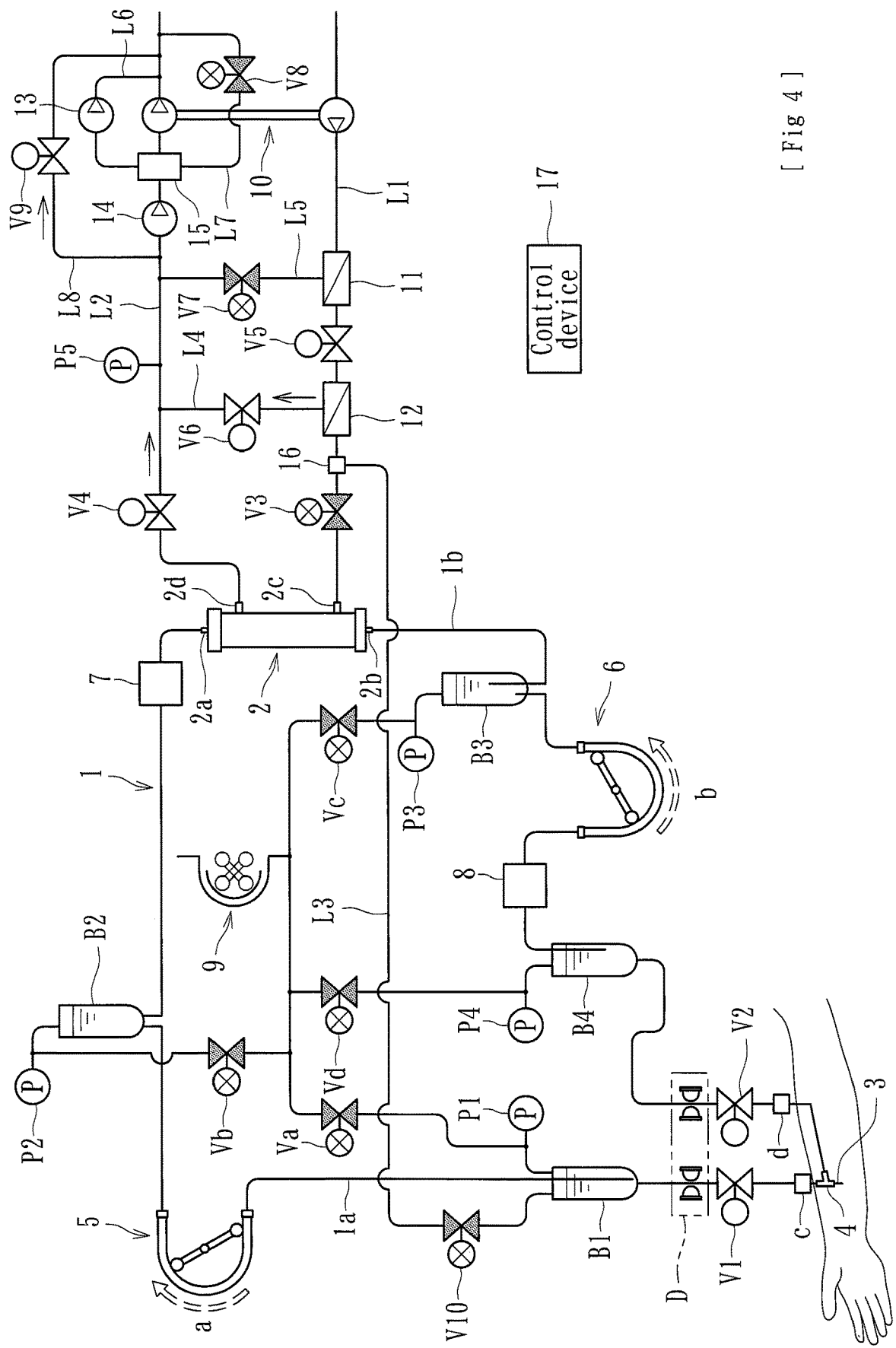
[Fig 4]

[Fig 5]

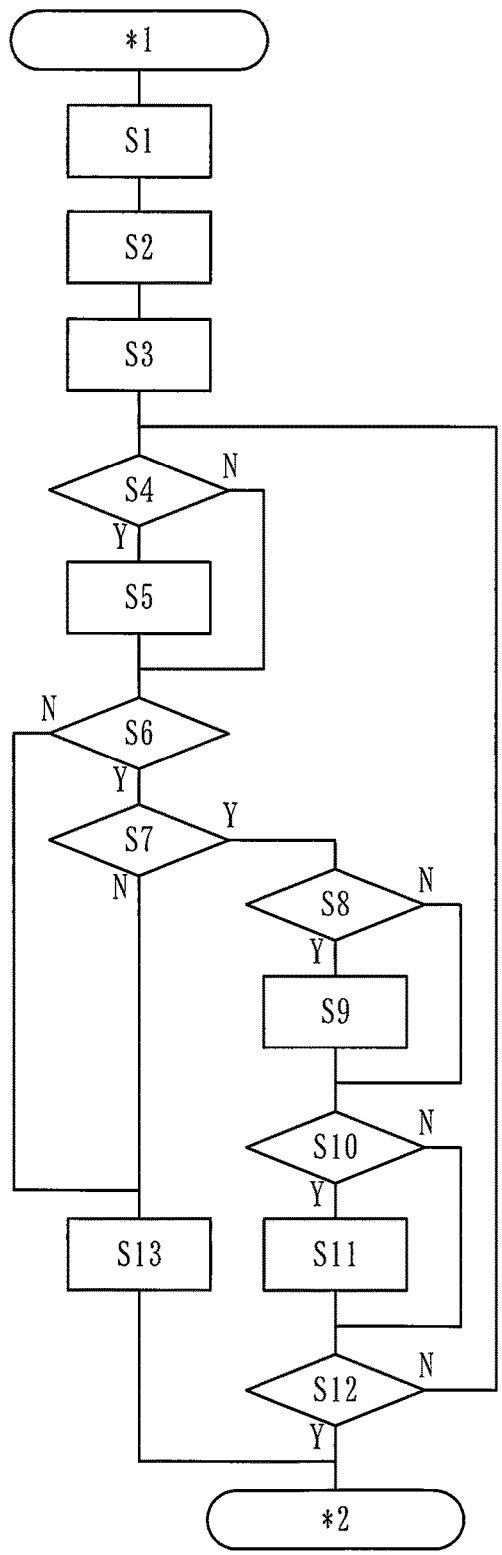

(∗1) Start blood removal (S1) Open atmosphere-releasing electromagnetic valve (S2) Rotate first blood pump in normal direction (S3) Rotate second blood pump in reverse direction (S4) Is P2 or P3 at or above warning point?

(S5) Reduce speeds of rotation of first blood pump and second blood pump (S6) Is P1 or P4 at or below warning point?

(S7) Is any blood detected?

(S8) Has first blood pump made predetermined number of revolutions?

(S9) Stop first blood pump (S10) Has second blood pump made predetermined number of revolutions?

(S11) Stop second blood pump (S12) Have first blood pump and second blood pump made predetermined number of revolutions?

(S13) Generate alarm notifying defect in blood removal (∗2) End blood removal

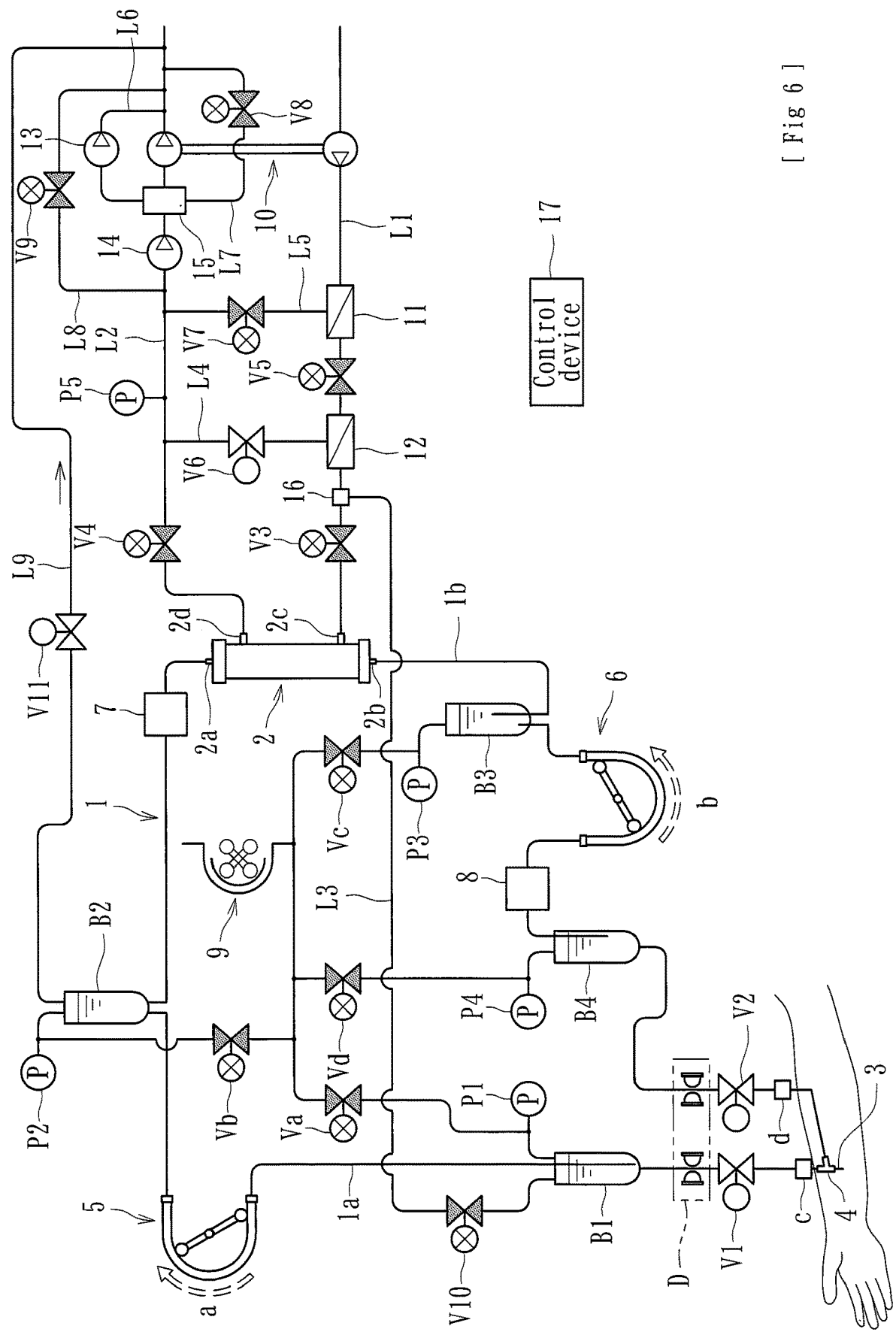
[Fig 6]

[Fig 7]

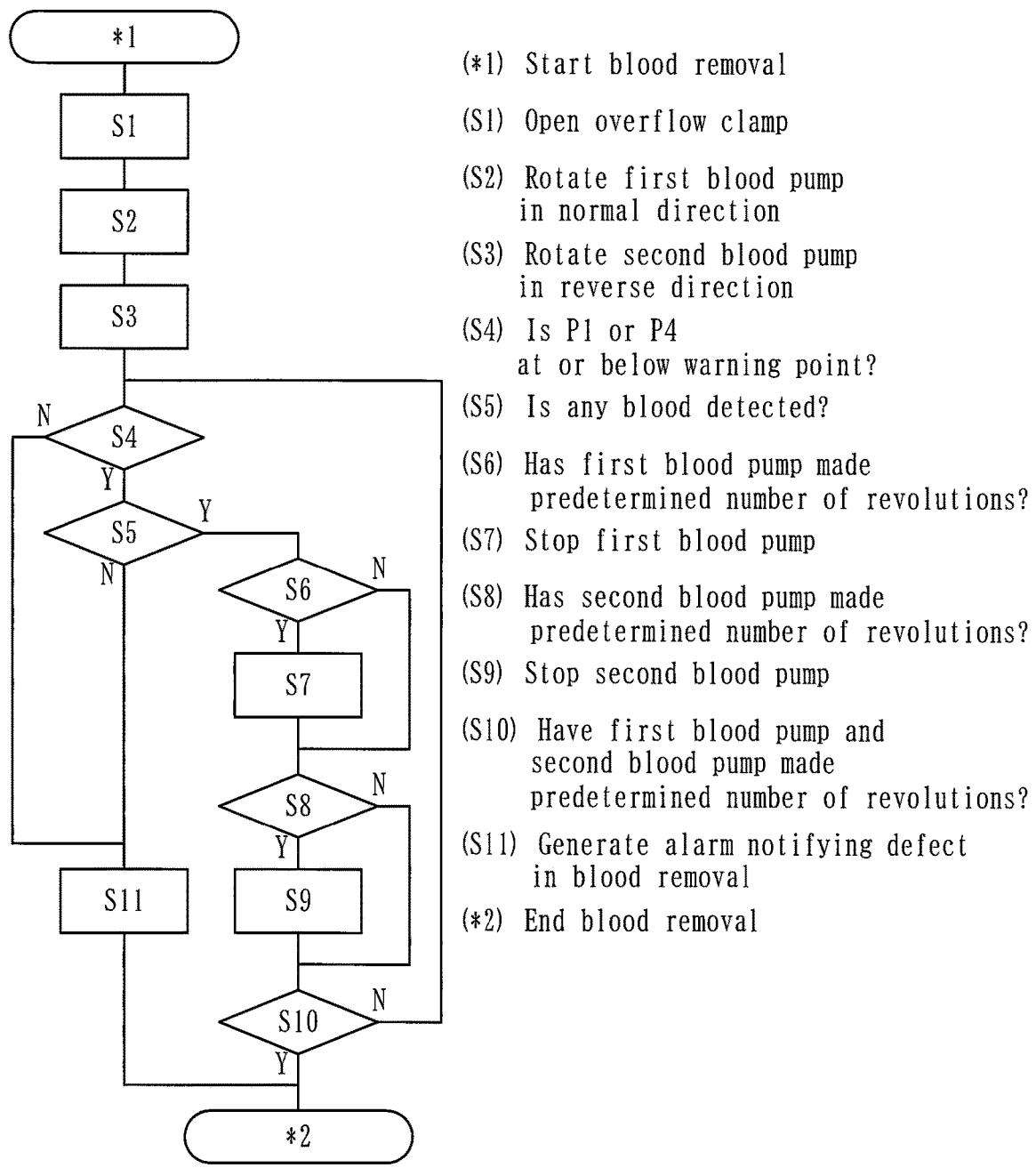

(*1) Start blood removal (S1) Open overflow clamp (S2) Rotate first blood pump in normal direction (S3) Rotate second blood pump in reverse direction (S4) Is P1 or P4 at or below warning point?

(S5) Is any blood detected?

(S6) Has first blood pump made predetermined number of revolutions?

(S7) Stop first blood pump (S8) Has second blood pump made predetermined number of revolutions?

(S9) Stop second blood pump (S10) Have first blood pump and second blood pump made predetermined number of revolutions?

(S11) Generate alarm notifying defect in blood removal (*2) End blood removal

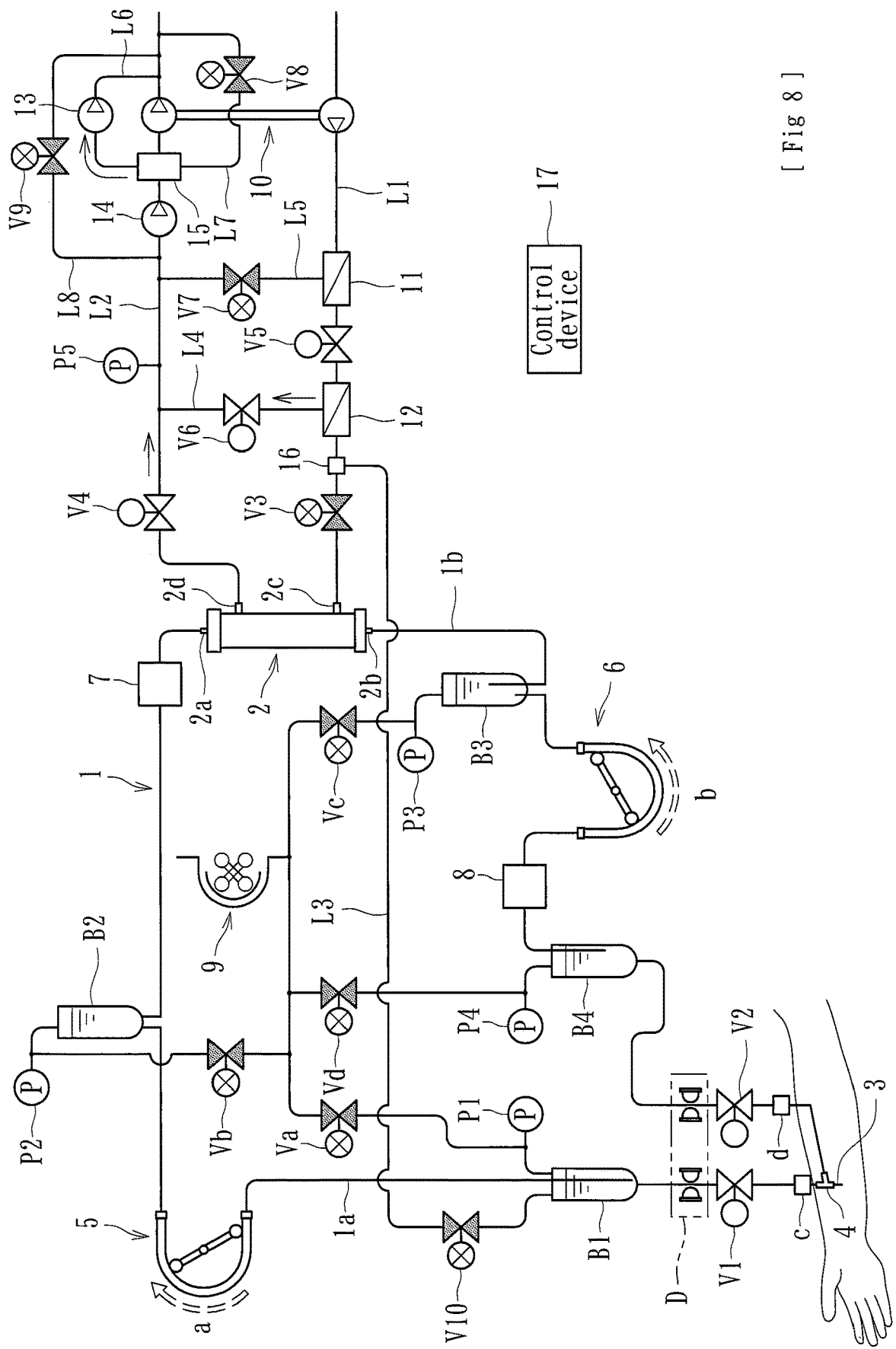
[Fig 8]

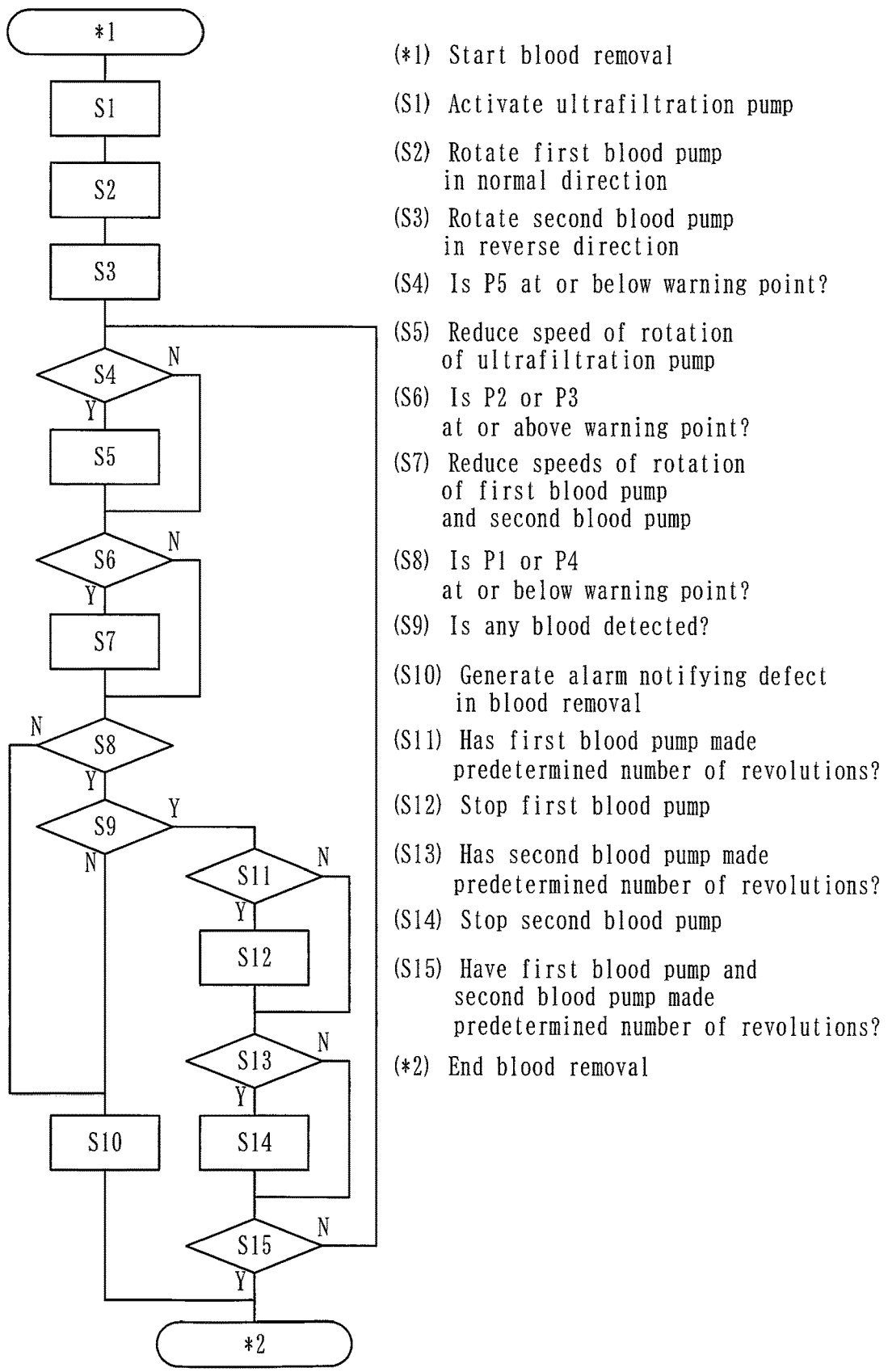

[Fig 9]

(*1) Start blood removal (S1) Activate ultrafiltration pump (S2) Rotate first blood pump in normal direction (S3) Rotate second blood pump in reverse direction (S4) Is P5 at or below warning point?

(S5) Reduce speed of rotation of ultrafiltration pump (S6) Is P2 or P3 at or above warning point?

(S7) Reduce speeds of rotation of first blood pump and second blood pump (S8) Is P1 or P4 at or below warning point?

(S9) Is any blood detected?

(S10) Generate alarm notifying defect in blood removal (S11) Has first blood pump made predetermined number of revolutions?

(S12) Stop first blood pump (S13) Has second blood pump made predetermined number of revolutions?

(S14) Stop second blood pump (S15) Have first blood pump and second blood pump made predetermined number of revolutions?

(*2) End blood removal

BLOOD PURIFICATION APPARATUS

FIELD

The present teachings relate to a blood purification apparatus for giving blood purification treatment while extracorporeally circulating the blood of a patient by using a single puncture needle.

BACKGROUND

In a general blood purification treatment, blood collected from a patient is extracorporeally circulated and is then returned to the body of the patient through a blood circuit. The blood circuit basically includes an arterial blood circuit and a venous blood circuit that are connectable to a dialyzer (a blood purification device) including, for example, hollow fiber membranes (blood purification membranes). The blood of the patient is purified by the dialyzer while being extracorporeally circulated through the blood circuit. Thus, the blood purification treatment is performed.

In a blood purification method called a single-needle double-pump method, an only puncture needle (a single needle) is connected to each of the distal ends of the arterial blood circuit and the venous blood circuit with a wye interposed therebetween, and the arterial blood circuit and the venous blood circuit are provided with respective peristaltic blood pumps. The two blood pumps are alternately activated to undergo normal rotation, whereby the blood of the patient is extracorporeally circulated through the blood circuit. Such a technique has not been disclosed by any publicly known invention, and there is no information on patent literature to be cited.

SUMMARY

The above known blood purification apparatus has the following problems.

Typically, prior to a blood purification treatment, a priming process is performed in which the blood circuit is filled with a priming solution and is thus cleaned. Therefore, at the start of the blood purification treatment (at the time of blood removal), the priming solution in the blood circuit needs to be substituted with blood. However, to prevent the priming solution substituted with blood from being introduced into the body of the patient at the time of blood removal a discharge port for discharging the priming solution, for example, needs to be provided near the distal end of the venous blood circuit. Furthermore, when the liquid flowing through the discharge port changes from the priming solution to the blood, the discharge port needs to be closed so that the blood removal is ended.

Some blood purification apparatuses may require a worker such as a medical staff to visually find the timing of change in the liquid flowing through the discharge port from the priming solution to the blood and to quickly close the discharge port at that timing so that blood purification treatment can be performed. This means that the medical staff needs to monitor the blood removal and perform the above work, making it difficult to automate the process of blood removal. If the blood purification apparatus employs a so-called double-needle method in which the arterial blood circuit and the venous blood circuit are provided with respective puncture needles or a so-called single-needle single-pump method in which the apparatus includes an only puncture needle and a blood pump that is provided only to the arterial blood circuit, it is possible, for example, to discharge, by using the blood pump, the priming solution substituted with the blood from the blood circuit through a dialysate drain line intended for discharging drain liquid from the dialyzer. However, if the blood purification apparatus employs the single-needle double-pump method, it is difficult to discharge the priming solution in, particularly, the venous blood circuit through the dialysate drain line because the venous blood circuit is provided with a second blood pump that stops the flow route.

The present invention has been conceived in view of the above circumstances and provides a blood purification apparatus employing a single-needle double-pump method in which an only puncture needle is connected to each of the distal ends of an arterial blood circuit and a venous blood circuit that are provided with respective peristaltic pumps, the blood purification apparatus being capable of automatically discharging a priming solution that has undergone substitution from the blood circuits during blood removal.

According to the teachings herein, there is provided a blood purification apparatus that performs blood purification treatment while extracorporeally circulating blood of a patient by using an only puncture needle. The apparatus includes a blood circuit including an arterial blood circuit and a venous blood circuit to respective distal ends of which the only puncture needle is connectable, the blood circuit allowing the blood of the patient to be extracorporeally circulated from the distal end of the arterial blood circuit to the distal end of the venous blood circuit; a blood purification device provided between the arterial blood circuit and the venous blood circuit and that purifies the blood flowing in the blood circuit; a first blood pump that is a peristaltic pump provided to the arterial blood circuit and is capable of introducing the blood of the patient into the blood circuit through the puncture needle when activated to undergo normal rotation; a second blood pump that is a peristaltic pump provided to the venous blood circuit and is capable of returning the blood in the blood circuit to the patient through the puncture needle when activated to undergo normal rotation; and a control device that allows the blood of the patient to be extracorporeally circulated through the blood circuit by causing the first blood pump and the second blood pump to alternately undergo normal rotation. During blood removal, the control device operates to substitute a priming solution in the blood circuit with the blood of the patient and to discharge the priming solution having undergone the substitution from the blood circuit by causing the first blood pump to undergo normal rotation and the second blood pump to undergo reverse rotation.

According to the teachings herein, in the blood purification apparatus taught herein, when the blood removal is performed, the control device activates the first blood pump and the second blood pump simultaneously.

According to the teachings herein, in the blood purification apparatus taught herein, a number of revolutions and a speed of rotation of each of the first blood pump and the second blood pump during the blood removal are set in accordance with a capacity of a portion between a site where the priming solution substituted with the blood is discharged and a site where a corresponding one of the first blood pump and the second blood pump is provided.

According to the teachings herein, in the blood purification apparatus taught herein, the blood purification device includes blood purification membranes that purify the blood and define blood flow routes in which the blood of the patient flows and dialysate flow routes in which a dialysate flows. Furthermore, during the blood removal, the control device causes the priming solution substituted with the blood to be discharged while being filtered from the blood flow routes into the dialysate flow routes.

According to the teachings herein, the blood purification apparatus taught herein further includes a pressure detection device capable of detecting a pressure generated when the priming solution substituted with the blood is discharged while being filtered from the blood flow routes into the dialysate flow routes. Furthermore, during the blood removal, the control device controls the first blood pump and the second blood pump on the basis of the pressure detected by the pressure detection device.

According to the teachings herein, in the blood purification apparatus taught herein, the blood circuit includes an overflow line provided between the first blood pump and the second blood pump. Furthermore, during the blood removal, the control device allows the priming solution substituted with the blood to be discharged through the overflow line.

According to the teachings herein, the blood purification apparatus taught herein further includes an ultrafiltration pump for removing water from the blood that is extracorporeally circulated through the blood circuit. Furthermore, during the blood removal, the control device allows the priming solution substituted with the blood to be discharged by activating the ultrafiltration pump.

According to the teachings herein, during the blood removal, the control device operates to substitute the priming solution in the blood circuit with the blood of the patient and to discharge the priming solution having undergone the substitution from the blood circuit by causing the first blood pump to undergo normal rotation and the second blood pump to undergo reverse rotation. Therefore, in a configuration employing a single-needle double-pump method in which an only puncture needle is connected to each of the distal ends of the arterial blood circuit and the venous blood circuit that are provided with the respective peristaltic pumps, the priming solution having undergone the substitution can be automatically discharged from the blood circuit during the blood removal.

According to the teachings herein, when the blood removal is performed, the control device activates the first blood pump and the second blood pump simultaneously. Therefore, the priming solution having undergone the substitution can be automatically discharged from the blood circuit during the blood removal. Moreover, the blood removal can be finished in a shorter time.

According to the teachings herein, the number of revolutions and the speed of rotation of each of the first blood pump and the second blood pump during the blood removal are set in accordance with the capacity of the portion between the site where the priming solution substituted with the blood is discharged and the site where a corresponding one of the first blood pump and the second blood pump is provided. Therefore, the priming solution having undergone the substitution can be discharged from the blood circuit more smoothly and more correctly.

According to the teachings herein, the blood purification device includes the blood purification membranes that purify the blood and define the blood flow routes in which the blood of the patient flows and the dialysate flow routes in which the dialysate flows. Furthermore, during the blood removal, the control device causes the priming solution substituted with the blood to be discharged while being filtered from the blood flow routes into the dialysate flow routes. Therefore, during the blood removal, the priming solution having undergone the substitution can be discharged automatically from the blood circuit by using the blood purification membranes of the blood purification device.

According to the teachings herein, the blood purification apparatus further includes the pressure detection device capable of detecting the pressure generated when the priming solution substituted with the blood is discharged while being filtered from the blood flow routes into the dialysate flow routes. Furthermore, during the blood removal, the control device controls the first blood pump and the second blood pump on the basis of the pressure detected by the pressure detection device. Therefore, the priming solution can be discharged from the blood circuit in accordance with the filtering capability of the blood purification membranes.

According to the teachings herein, the blood circuit includes the overflow line provided between the first blood pump and the second blood pump. Furthermore, during the blood removal, the control device allows the priming solution substituted with the blood to be discharged through the overflow line. Therefore, the priming solution can be smoothly discharged from the blood circuit without using the blood purification membranes or the like.

According to the teachings herein, the blood purification apparatus further includes the ultrafiltration pump for removing water from the blood that is extracorporeally circulated through the blood circuit. Furthermore, during the blood removal, the control device allows the priming solution substituted with the blood to be discharged by activating the ultrafiltration pump. Therefore, during the blood removal, the priming solution having undergone the substitution can be discharged automatically from the blood circuit by using the ultrafiltration pump.

BRIEF DESCRIPTION OF THE DRAWINGS

FIG. 1 is a schematic diagram of a blood purification apparatus according to the present teachings.

FIG. 2 is a schematic view of an only puncture needle (a single needle) included in the blood purification apparatus.

FIG. 3 is a schematic view of a blood purification device included in the blood purification apparatus.

FIG. 4 is a schematic diagram illustrating a state of the blood purification apparatus during blood removal.

FIG. 5 is a flow chart illustrating a control process performed by a control device, included in the blood purification apparatus, during blood removal.

FIG. 6 is a schematic diagram of a blood purification apparatus (in a state during blood removal) according to the present teachings.

FIG. 7 is a flow chart illustrating a control process performed by a control device, included in the blood purification apparatus, during blood removal.

FIG. 8 is a schematic diagram of a blood purification apparatus (in a state during blood removal) according to the present teachings.

FIG. 9 is a flow chart illustrating a control process performed by a control device, included in the blood purification apparatus, during blood removal.

DETAILED DESCRIPTION

Embodiments of the present invention will now be described specifically with reference to the drawings.

A blood purification apparatus according to a first embodiment is a dialysis apparatus for giving a hemodialysis treatment and includes, as illustrated in FIG. 1, a blood circuit 1 including an arterial blood circuit 1a and a venous blood circuit 1b, a dialyzer 2 (a blood purification device) provided between the arterial blood circuit 1a and the venous blood circuit 1b and that purifies blood flowing in the blood circuit, a first blood pump 5 that is a peristaltic pump and is provided to the arterial blood circuit 1a, a second blood pump 6 that is a peristaltic pump and is provided to the venous blood circuit 1b, hematocrit sensors 7 and 8, and a control device 17.

As illustrated in FIG. 2, an only puncture needle 3 (a single needle) is connectable to each of the distal ends of the arterial blood circuit 1a and the venous blood circuit 1b with a wye 4 interposed therebetween. The puncture needle 3 is stuck into an accessing unit, such as a shunt placed in a patient, whereby the blood of the patient is allowed to be extracorporeally circulated. As illustrated in FIG. 2, the other end of the wye 4 branches into two, to which flexible tubes (a) and (b) are connected, respectively. The flexible tube (a) is provided with a connector (c) to which the distal end of the arterial blood circuit 1a is connected. The flexible tube (b) is provided with a connector (d) to which the distal end of the venous blood circuit 1b is connected. The connectors (c) and d according to the first embodiment each include a luer taper and a screw that are connectable to the distal end of a corresponding one of the arterial blood circuit 1a and the venous blood circuit 1b. The distal ends of the arterial blood circuit 1a and the venous blood circuit 1b are lockable in a state connected to the connectors (c) and (d).

The dialyzer 2 has, in a housing thereof, a blood inlet 2a (a blood introduction port), a blood outlet 2b (a blood delivery port), a dialysate inlet 2c (an inlet of the dialysate flow route, or a dialysate introduction port), and a dialysate outlet 2d (an outlet of the dialysate flow route, or a dialysate delivery port). The proximal end of the arterial blood circuit 1a is connected to the blood inlet 2a. The proximal end of the venous blood circuit 1b is connected to the blood outlet 2b. The dialysate inlet 2c and the dialysate outlet 2d are connected to a dialysate introduction line L1 and a dialysate drain line L2, respectively, extending from the body of the dialysis apparatus.

As illustrated in FIG. 3, the dialyzer 2 houses a plurality of hollow fiber membranes M, which serve as blood purification membranes for purifying the blood. More specifically, blood flow routes ($\alpha$) are provided on the inside of the respective hollow fiber membranes (M), and dialysate flow routes ($\beta$) are provided on the outside of the hollow fiber membranes (M) (between the outer peripheral surface of each of the hollow fiber membranes (M) and the inner peripheral surface of a case C forming the housing). The hollow fiber membranes (M) each have a number of very small holes (pores) extending therethrough from the outer peripheral surface to the inner peripheral surface.

Thus, the blood flow routes ($\alpha$) in which the blood of the patient flows and the dialysate flow routes ($\beta$) in which the dialysate flows are defined by the hollow fiber membranes M. The blood flowing from the arterial blood circuit 1a enters the blood flow routes ($\alpha$) and flows into the venous blood circuit 1b, whereas the dialysate flowing from the dialysate introduction line L1 enters the dialysate flow routes ($\beta$) and flows into the dialysate drain line L2, whereby impurities and the like contained in the blood are allowed to be filtered through the hollow fiber membranes (M) into the dialysate.

The arterial blood circuit 1a is provided with an air-trap chamber B1 in a portion thereof on the upstream side with respect to the first blood pump 5 (between the first blood pump 5 and the puncture needle 3). The venous blood circuit 1b is provided with an air-trap chamber B4 in a portion thereof on the downstream side with respect to the second blood pump 6 (between the second blood pump 6 and the puncture needle 3). Furthermore, the arterial blood circuit 1a is provided with a dialyzer-inlet-pressure chamber B2 in a portion thereof on the downstream side with respect to the first blood pump 5 (between the first blood pump 5 and the dialyzer 2). The venous blood circuit 1b is provided with a dialyzer-outlet-pressure chamber B3 in a portion thereof on the upstream side with respect to the second blood pump 6 (between the second blood pump 6 and the dialyzer 2).

The air-trap chambers B1 and B4, the dialyzer-inlet-pressure chamber B2, and the dialyzer-outlet-pressure chamber B3 are each configured such that an air layer can be formed on the upper side of the space provided therein and a liquid layer can be formed on the lower side of the space provided therein. The chambers B1 to B4 are provided with respective pressure detection devices (P1 to P4) that are each capable of detecting the hydraulic pressure in the liquid layer by detecting the pressure in the air layer. In the first embodiment, the dialyzer-inlet-pressure chamber B2 and the dialyzer-outlet-pressure chamber B3 each have a greater capacity than each of the air-trap chambers B1 and B4.

The air-trap chambers B1 and B4, the dialyzer-inlet-pressure chamber B2, and the dialyzer-outlet-pressure chamber B3 according to the first embodiment are provided with respective air flow routes extending from the tops thereof. Air is allowed to flow through the air flow routes, which are openable and closable by respective electromagnetic valves Va to Vd. The air flow routes are connected, on the distal side thereof, to a liquid-level-adjusting device 9 that is a peristaltic pump. When the liquid-level-adjusting device 9 is rotated in the normal direction or in the reverse direction while any of the electromagnetic valves Va to Vd are opened, the level of the liquid surface in corresponding ones of the chambers (the air-trap chambers B1 and B4, the dialyzer-inlet-pressure chamber B2, and the dialyzer-outlet-pressure chamber B3) can be raised or lowered.

On the other hand, the arterial blood circuit 1a is provided on the distal side thereof (between the air-trap chamber B1 and the puncture needle 3) with a clamping device V1 capable of opening and closing the flow route provided by the arterial blood circuit 1a. Furthermore, the venous blood circuit 1b is provided on the distal side thereof (between the air-trap chamber B4 and the puncture needle 3) with a clamping device V2 capable of opening and closing the flow route provided by the venous blood circuit 1b. Furthermore, air-bubble detection devices D capable of detecting air bubbles in the liquid are provided on the downstream side with respect to the clamping device V1 (between the clamping device V1 and the air-trap chamber B1) and on the upstream side with respect to the clamping device V2 (between the clamping device V2 and the air-trap chamber B4).

Furthermore, the arterial blood circuit 1a and the venous blood circuit 1b are provided with the hematocrit sensors 7 and 8 at a position between the dialyzer-inlet-pressure chamber B2 and the dialyzer 2 and at a position between the second blood pump 6 and the air-trap chamber B4, respectively. The hematocrit sensors 7 and 8 each include, for example, a light-emitting element such as an LED and a light-receiving element such as a photodiode. The light-emitting element applies light at a predetermined wavelength to the blood, and the light-receiving element receives the light transmitted through or reflected by the blood, whereby the hematocrit value representing the concentration of the blood of the patient flowing in the blood circuit 1 is measured. That is, the hematocrit value is a benchmark representing the blood concentration and is specifically expressed by the ratio of volume of red blood cells with respect to the total volume of the blood. In the first embodiment, the rate of change in the circulating blood volume (ΔBV) can be obtained on the basis of the hematocrit values detected by the hematocrit sensors 7 and 8. The hematocrit sensors 7 and 8 are also capable of detecting the occurrence of recirculation in which the blood returned to the patient through the puncture needle 3 is collected again from the puncture needle 3 during the treatment.

The first blood pump 5 is provided at a position of the arterial blood circuit 1a that is between the air-trap chamber B1 and the dialyzer-inlet-pressure chamber B2. The first blood pump 5 is a peristaltic pump capable of undergoing normal rotation (the rotation for the treatment) and reverse rotation (the rotation opposite to the rotation for the treatment). When the first blood pump 5 undergoes normal rotation (rotates in a direction a indicated in FIG. 1), the blood of the patient can be introduced into the blood circuit 1 (the blood of the patient can be collected and introduced into the blood circuit 1) through the puncture needle 3. The direction of rotation and the speed of rotation (the flow rate) of the first blood pump 5 according to the first embodiment are appropriately controllable by the control device 17.

The second blood pump 6 is provided at a position of the venous blood circuit 1b that is between the dialyzer-outlet-pressure chamber B3 and the air-trap chamber B4. The second blood pump 6 is a peristaltic pump capable of undergoing normal rotation (the rotation for the treatment) and reverse rotation (the rotation opposite to the rotation for the treatment). When the second blood pump 6 undergoes normal rotation (rotates in a direction (a) indicated in FIG. 1), the blood in the blood circuit 1 can be returned to the patient (the blood that has been extracorporeally circulated through the blood circuit 1 can be returned to the patient) through the puncture needle 3. The direction of rotation and the speed of rotation (the flow rate) of the second blood pump 6 according to the first embodiment are appropriately controllable by the control device 17.

Hence, in the blood purification treatment, when the first blood pump 5 is activated to undergo normal rotation while the second blood pump 6 is stopped, the blood of the patient is introduced into the arterial blood circuit 1a through the puncture needle 3, undergoes bubble removal in the air-trap chamber B1, and flows into the dialyzer 2, where the blood is purified. While the blood of the patient that has been introduced into the blood circuit 1 flows through the flow route provided by the arterial blood circuit 1a and the venous blood circuit 1b and extending up to the second blood pump 6, the blood flows into the dialyzer-inlet-pressure chamber B2 and into the dialyzer-outlet-pressure chamber B3 and is stored therein by respective predetermined capacities.

Subsequently, the second blood pump 6 is activated to undergo normal rotation while the first blood pump 5 is stopped. Accordingly, the blood having flowed through the flow route provided by the arterial blood circuit 1a and the venous blood circuit 1b and extending up to the position where the second blood pump 6 is provided and the blood having flowed into the dialyzer-inlet-pressure chamber B2 and into the dialyzer-outlet-pressure chamber B3 flow into the air-trap chamber B4 and undergo bubble removal therein. Then, the resulting blood is returned to the patient through the puncture needle 3. Thus, by alternately activating the first blood pump 5 and the second blood pump 6 to undergo normal rotation, blood purification treatment can be performed while the blood of the patient is extracorporeally circulated by using the only puncture needle 3.

As described above, the end of the dialysate introduction line L1 and the end of the dialysate drain line L2 are connected to the dialysate inlet 2c and the dialysate outlet 2d, respectively, of the dialyzer 2. Furthermore, a duplex pump 10 is provided over the dialysate introduction line L1 and the dialysate drain line L2. When the duplex pump 10 is activated, a dialysate prepared to have a predetermined concentration is introduced into the dialyzer 2 and the dialysate having undergone dialysis is discharged from the dialyzer 2.

The dialysate introduction line L1 is provided with an electromagnetic valve V3 at a halfway position thereof (on the downstream side (i.e., on the side of the dialyzer 2) with respect to the connection between the dialysate introduction line L1 and a connection line L3). The dialysate drain line L2 is provided with an electromagnetic valve V4 at a halfway position thereof (on the upstream side (i.e., on the side of the dialyzer 2) with respect to the connection between the dialysate drain line L2 and a bypass line L4). The dialysate introduction line L1 is further provided with filtration filters 11 and 12 at positions thereof between the duplex pump 10 and the electromagnetic valve V3.

The filtration filters 11 and 12 are intended for filtering and thus purifying the dialysate flowing in the dialysate introduction line L1. A bypass line L5 and the bypass line L4 are connected to the filtration filters 11 and 12, respectively, so as to introduce the dialysate into the dialysate drain line L2 to which the bypass lines L5 and L4 are connected. The bypass lines L5 and L4 are provided with electromagnetic valves V7 and V6, respectively. Furthermore, an electromagnetic valve V5 is provided at a position of the dialysate introduction line L1 that is between the filtration filter 11 and the filtration filter 12.

On the other hand, the dialysate drain line L2 is provided with a pressure detection device (hydraulic-pressure-measuring device) P5 at a position thereof between the connection to the bypass line L4 and the connection to the bypass line L5. The pressure detection device P5 is capable of measuring the hydraulic pressure of the dialysate. Furthermore, a bypass line L6 and an atmosphere release line L8 that bypass the duplex pump 10 are connected to the dialysate drain line L2. The bypass line L6 is provided with an ultrafiltration pump 13 for removing water from the blood of the patient flowing in the dialyzer 2. The atmosphere release line L8 is provided with an atmosphere-releasing electromagnetic valve V9 capable of opening and closing the relevant flow route.

Furthermore, the dialysate drain line L2 is provided with a pump 14 at a position thereof on the upstream side with respect to the duplex pump 10 (between the connection to the atmosphere release line L8 and the duplex pump 10). The pump 14 adjusts the hydraulic pressure on the drain-liquid side of the duplex pump 10. Furthermore, the dialysate drain line L2 is provided with a degassing chamber 15 at a position on the upstream side with respect to the duplex pump 10 (between the pump 14 and the duplex pump 10). A degassing line L7 is connected to the degassing chamber 15 with a check valve or the like interposed therebetween. The degassing line L7 is provided with a degassing electromagnetic valve V8.

The connection line L3 is connected at one end thereof to a collecting port 16 (a sampling port) provided at a predetermined point of the dialysate introduction line L1 (in the first embodiment, a point between the electromagnetic valve V3 and the filtration filter 12). The connection line L3 is also connected at the other end thereof to the air-trap chamber B1 provided to the arterial blood circuit 1a (or the air-trap chamber B4 provided to the venous blood circuit 1b). Thus, the connection line L3 provides a flow route through which the dialysate flowing in the dialysate introduction line L1 is allowed to be supplied to the arterial blood circuit 1a (or to the venous blood circuit 1b). The connection line L3 is provided with an electromagnetic valve V10. When the electromagnetic valve V10 is opened, the dialysate in the dialysate introduction line L1 can be supplied to the blood circuit 1.

Hence, at the time of priming that is performed before the blood purification treatment, the distal end of the arterial blood circuit 1a and the distal end of the venous blood circuit 1b are connected to each other so that a closed circuit is formed, and the electromagnetic valve V10 is opened, whereby the dialysate in the dialysate introduction line L1 is supplied as a priming solution to the blood circuit 1. While the connection line L3 according to the first embodiment is connected to the top of the air-trap chamber B1 (or the air-trap chamber B4), the connection line L3 may be connected to any other point of the arterial blood circuit 1a or the venous blood circuit 1b.

The control device 17 is capable of controlling the opening and closing of the devices such as the clamping devices V1 and V2 and the electromagnetic valves V3 to V10 (as well as the electromagnetic valves Va to Vd), the operation of the actuators included in the devices such as the duplex pump 10, the first blood pump 5, and the second blood pump 6 (as well as the liquid-level-adjusting device 9), and so forth. The control device 17 is, for example, a microcomputer or the like. As described above, during the blood purification treatment, the control device 17 activates the first blood pump 5 and the second blood pump 6 alternately to undergo normal rotation, thereby performing the purification treatment while extracorporeally circulating the blood of the patient.

As illustrated in FIG. 4, during blood removal, the control device 17 according to the first embodiment causes the first blood pump 5 to undergo normal rotation (the rotation in the direction a) and the second blood pump 6 to undergo reverse rotation (the rotation in a direction b), whereby the priming solution (the dialysate in the first embodiment, or a physiological saline solution) in the blood circuit 1 is substituted with the blood of the patient, and the priming solution thus substituted is discharged from the blood circuit 1. The blood removal refers to a process performed after the priming process, in which the blood circuit 1 is filled with the priming solution, and before the blood purification treatment and in which the priming solution is substituted with the blood of the patient.

More specifically, at the time of blood removal, the control device 17 activates the first blood pump 5 and the second blood pump 6 simultaneously such that the first blood pump 5 undergoes normal rotation while the second blood pump 6 undergoes reverse rotation. Thus, the blood is introduced from the body of the patient into the blood circuit 1 through the puncture needle 3, and the priming solution is substituted with the blood. The priming solution thus substituted is discharged from the blood circuit 1 while being filtered through the hollow fiber membranes M (the blood purification membranes) in the dialyzer 2 from the blood flow routes ($\alpha$) into the dialysate flow routes ($\beta$). The priming solution filtered into the dialysate flow routes ($\beta$) flows through the dialysate drain line L2 and then through the atmosphere release line L8 and is discharged to the outside.

In the first embodiment, to filter the thus substituted priming solution through the hollow fiber membranes (M) (the blood purification membranes) of the dialyzer 2 from the blood flow routes $\alpha$ into the dialysate flow routes ($\beta$), the ultrafiltration pump 13 is stopped while the duplex pump 10 is activated with the atmosphere-releasing electromagnetic valve V9 being open as illustrated in FIG. 4 (and with the electromagnetic valves V4, V5, and V6 also being open but with the electromagnetic valves V3 and V7 and the degassing electromagnetic valve V8 being closed), whereby the priming solution filtered into the dialysate flow routes ($\beta$) flows through the dialysate drain line L2. Alternatively, for example, the duplex pump 10 may be stopped.

In the first embodiment, the number of revolutions and the speed of rotation of each of the first blood pump 5 and the second blood pump 6 during the blood removal are set in accordance with the capacity (the priming volume) of a portion between a site where the priming solution substituted with the blood is discharged (in the first embodiment, the site where the dialyzer 2 is provided) and a site where a corresponding one of the first blood pump 5 and the second blood pump 6 is provided. That is, the time of blood removal by the normal rotation of the first blood pump 5 and the time of blood removal by the reverse rotation of the second blood pump 6 can be made substantially equal, avoiding a situation where the blood removal by the second blood pump 6 is not complete even if the blood removal by the first blood pump 5 is complete or a situation where the blood removal by the first blood pump 5 is not complete even if the blood removal by the second blood pump 6 is complete.

In the first embodiment, the pressure generated when the priming solution substituted with the blood is filtered from the blood flow routes ($\alpha$) into the dialysate flow routes ($\beta$) and is discharged is detectable by the pressure detection devices (P1 to P4). Furthermore, during the blood removal, the control device 17 controls the operation of the first blood pump 5 and the second blood pump 6 on the basis of the pressures detected by the pressure detection devices (P1 to P4). Therefore, if the pressure generated when the priming solution is filtered from the blood flow routes $\alpha$ into the dialysate flow routes $\beta$ is increased during the blood removal, the number of revolutions and the speed of rotation of each of the first blood pump 5 and the second blood pump 6 are reduced, so that the occurrence of damage to the hollow fiber membranes (filtering membranes) can be suppressed.

Now, a control process (a process of controlling the blood removal) performed by the control device 17 according to the first embodiment will be described with reference to the flow chart illustrated in FIG. 5. Note that, prior to the blood removal, the priming process is performed, and the blood circuit 1 is thus filled with the priming solution.

When the process of blood removal is started after the priming process, the atmosphere-releasing electromagnetic valve V9 is opened in step S1 and the first blood pump 5 is rotated in the normal direction (step S2) while the second blood pump 6 is rotated in the reverse direction (step S3).

Subsequently, whether or not either of the values detected by the pressure detection devices P2 and P3 is at or above a warning point is checked (step S4). If it is determined that either of the values is at or above the warning point, the speeds of rotation of the first blood pump 5 and the second blood pump 6 are reduced (step S5). If it is determined that neither of the values is at or above the warning point, step S5 is skipped and the process proceeds to step S6. Then, whether or not either of the values detected by the pressure detection devices P1 and P4 is at or below the warning point is checked (step S6). If it is determined that either of the values is at or below the warning point, the process proceeds to step S13, where an alarm notifying a defect in blood removal is generated, and the blood removal is ended. If it is determined in step S6 that neither of the values is at or below the warning point, the process proceeds to step S7, where whether or not the hematocrit sensors 7 and 8 have detected any blood within a predetermined period of time is checked. If no blood is detected, the process proceeds to step S13, where an alarm notifying a defect in blood removal is generated, and the blood removal is ended.

If the hematocrit sensors 7 and 8 have detected any blood within the predetermined period of time in step S7, whether or not the first blood pump 5 has made a predetermined number of revolutions (corresponding to the capacity (the priming volume) of the portion between the site where the priming solution substituted with the blood is discharged (in the first embodiment, the site where the dialyzer 2 is provided) and the site where the first blood pump 5 is provided) is checked (step S8). If it is determined that the first blood pump 5 has made the predetermined number of revolutions, the first blood pump 5 is stopped in step S9. Then, the process proceeds to step S10. If it is determined in step S8 that the first blood pump 5 has not made the predetermined number of revolutions yet, step S9 is skipped. Then, whether or not the second blood pump 6 has made a predetermined number of revolutions (corresponding to the capacity (the priming volume) of the portion between the site where the priming solution substituted with the blood is discharged (in the first embodiment, the site where the dialyzer 2 is provided) and the site where the second blood pump 6 is provided) is checked (step S10).

If it is determined in step S10 that the second blood pump 6 has made the predetermined number of revolutions, the second blood pump 6 is stopped in step S11. Then, the process proceeds to step S12. If it is determined in step S10 that the second blood pump 6 has not made the predetermined number of revolutions yet, step S11 is skipped. Then, whether or not the first blood pump 5 and the second blood pump 6 each have made a predetermined number of revolutions is checked (step S12). If it is determined in step S12 that the first blood pump 5 and the second blood pump 6 each have not made the predetermined number of revolutions yet, the process returns to step S4. Then, the above series of control steps are performed again. If it is determined that the first blood pump 5 and the second blood pump 6 each have made the predetermined number of revolutions, the blood removal is ended. Thus, the whole process of blood removal is ended.

According to the first embodiment, during the blood removal, the control device 17 causes the first blood pump 5 to undergo normal rotation and the second blood pump 6 to undergo reverse rotation, whereby the priming solution in the blood circuit 1 is substituted with the blood of the patient, and the priming solution thus substituted is discharged from the blood circuit 1. Therefore, in a configuration employing the single-needle double-pump method in which the only puncture needle 3 is connected to each of the distal ends of the arterial blood circuit 1a and the venous blood circuit 1b that are provided with the respective peristaltic pumps (the first blood pump 5 and the second blood pump 6), the priming solution having undergone the substitution can be automatically discharged from the blood circuit 1 during the blood removal.

The control device 17 according to the first embodiment activates the first blood pump 5 and the second blood pump 6 simultaneously at the time of blood removal. Therefore, the priming solution having undergone the substitution can be automatically discharged from the blood circuit 1 during the blood removal. Moreover, the blood removal can be finished in a shorter time. Furthermore, according to the first embodiment, the number of revolutions and the speed of rotation of each of the first blood pump 5 and the second blood pump 6 during the blood removal are set in accordance with the capacity of the portion between the site where the priming solution substituted with the blood is discharged (the site where the dialyzer 2 is provided) and the site where a corresponding one of the first blood pump 5 and the second blood pump 6 is provided. Therefore, the priming solution having undergone the substitution can be discharged from the blood circuit 1 more smoothly and more correctly.

According to the first embodiment, the dialyzer 2 (the blood purification device) includes the hollow fiber membranes (M) (the blood purification membranes) for purifying blood and that define the blood flow routes ($\alpha$) in which the blood of the patient flows and the dialysate flow routes ($\beta$) in which the dialysate flows. Furthermore, the control device 17 causes the priming solution substituted with the blood to be filtered from the blood flow routes ($\alpha$) into the dialysate flow routes $\beta$ and is then discharged during the blood removal. Therefore, during the blood removal, the priming solution having undergone the substitution can be discharged automatically from the blood circuit 1 by using the blood purification membranes of the blood purification device (the hollow fiber membranes (M) of the dialyzer 2).

Furthermore, the blood purification apparatus includes the pressure detection devices (P1 to P4) capable of detecting the pressure generated when the priming solution substituted with the blood is discharged while being filtered from the blood flow routes $\alpha$ into the dialysate flow routes ($\beta$). Furthermore, during the blood removal, the control device 17 controls the operation of the first blood pump 5 and the second blood pump 6 on the basis of the pressures detected by the pressure detection devices (P1 to P4). Therefore, the priming solution can be discharged from the blood circuit 1 in accordance with the filtering capability of the blood purification membranes (the hollow fiber membranes M of the dialyzer 2).

Now a second embodiment of the present invention will be described.

A blood purification apparatus according to the second embodiment is a dialysis apparatus for giving a hemodialysis treatment, as in the first embodiment, and includes, as illustrated in FIG. 6, a blood circuit 1 including an arterial blood circuit 1a and a venous blood circuit 1b, a dialyzer 2 (a blood purification device) provided between the arterial blood circuit 1a and the venous blood circuit 1b and that purifies blood flowing in the blood circuit, a first blood pump 5 that is a peristaltic pump and is provided to the arterial blood circuit 1a, a second blood pump 6 that is a peristaltic pump and is provided to the venous blood circuit 1b, hematocrit sensors 7 and 8, a control device 17, and an overflow line L9. Elements that are the same as those described in the first embodiment are denoted by corresponding ones of the reference numerals, and detailed description of those elements is omitted.

As illustrated in FIG. 6, the overflow line L9 forms a flow route provided between the first blood pump 5 and the second blood pump 6 in the blood circuit 1. The overflow line L9 according to the second embodiment extends from the top of the dialyzer-inlet-pressure chamber B2, with the other end thereof connected to a position of the dialysate drain line L2 that is on the downstream side with respect to the duplex pump 10. The overflow line L9 is provided with an overflow clamp V11 that is an electromagnetic valve. The overflow clamp V11 is controllable by the control device 17 so as to open and close the overflow line L9 as appropriate.

As in the first embodiment, during the blood removal, the control device 17 according to the second embodiment causes the first blood pump 5 to undergo normal rotation (the rotation in the direction a) and the second blood pump 6 to undergo reverse rotation (the rotation in the direction b), whereby the priming solution (the dialysate in the second embodiment, or a physiological saline solution) in the blood circuit 1 is substituted with the blood of the patient, and the priming solution thus substituted is discharged from the blood circuit 1.

More specifically, the control device 17 activates the first blood pump 5 and the second blood pump 6 simultaneously such that the first blood pump 5 undergoes normal rotation while the second blood pump 6 undergoes reverse rotation. Thus, the blood of the patient is introduced from the body of the patient into the blood circuit 1 through the puncture needle 3, and the priming solution is substituted with the blood. Furthermore, with the overflow clamp V11 being open, the priming solution thus substituted is discharged through the overflow line L9.

In the second embodiment, to discharge the priming solution having undergone the substitution to the outside through the overflow line L9, while the ultrafiltration pump 13 and the duplex pump 10 are stopped, the overflow clamp V11 is opened as illustrated in FIG. 6 (with the electromagnetic valve V6 being open, the electromagnetic valves V3, V4, V5, and V7 and the degassing electromagnetic valve V8 being closed, and the atmosphere-releasing electromagnetic valve V9 being closed). Thus, the priming solution is allowed to flow through the dialysate drain line L2 via the overflow line L9. Alternatively, for example, the duplex pump 10 may be activated.

In the second embodiment, the number of revolutions and the speed of rotation of each of the first blood pump 5 and the second blood pump 6 during the blood removal are set in accordance with the capacity (the priming volume) of a portion between a site where the priming solution substituted with the blood is discharged (in the second embodiment, the site where the dialyzer-inlet-pressure chamber B2 is provided) and a site where a corresponding one of the first blood pump 5 and the second blood pump 6 is provided. That is, the time of blood removal by the normal rotation of the first blood pump 5 and the time of blood removal by the reverse rotation of the second blood pump 6 can be made substantially equal, avoiding a situation where the blood removal by the second blood pump 6 is not complete even if the blood removal by the first blood pump 5 is complete or a situation where the blood removal by the first blood pump 5 is not complete even if the blood removal by the second blood pump 6 is complete.

Now, a control process (a process of controlling the blood removal) performed by the control device 17 according to the second embodiment will be described with reference to the flow chart illustrated in FIG. 7. Note that, prior to the blood removal, the priming process is performed, and the blood circuit 1 is thus filled with the priming solution.

When the process of blood removal is started after the priming process, the overflow clamp V11 is opened in step S1 and the first blood pump 5 is rotated in the normal direction (step S2) while the second blood pump 6 is rotated in the reverse direction (step S3).

Subsequently, whether or not either of the values detected by the pressure detection devices P1 and P4 is at or below a warning point is checked (step S4). If it is determined that either of the values is at or below the warning point, the process proceeds to step S11, where an alarm notifying a defect in blood removal is generated, and the blood removal is ended. If it is determined in step S4 that neither of the values is at or below the warning point, the process proceeds to step S5, where whether or not the hematocrit sensors 7 and 8 have detected any blood is checked. If no blood is detected, the process proceeds to step S11, where an alarm notifying a defect in blood removal is generated, and the blood removal is ended.

If the hematocrit sensors 7 and 8 have detected any blood within the predetermined period of time in step S5, whether or not the first blood pump 5 has made a predetermined number of revolutions (corresponding to the capacity (the priming volume) of the portion between the site where the priming solution substituted with the blood is discharged (in the second embodiment, the site where the dialyzer-inlet-pressure chamber B2 is provided) and the site where the first blood pump 5 is provided) is checked (step S6). If it is determined that the first blood pump 5 has made the predetermined number of revolutions, the first blood pump 5 is stopped in step S7. Then, the process proceeds to step S8. If it is determined in step S6 that the first blood pump 5 has not made the predetermined number of revolutions yet, step S7 is skipped. Then, whether or not the second blood pump 6 has made a predetermined number of revolutions (corresponding to the capacity (the priming volume) of the portion between the site where the priming solution substituted with the blood is discharged (in the second embodiment, the site where the dialyzer-inlet-pressure chamber B2 is provided) and the site where the second blood pump 6 is provided) is checked (step S8).

If it is determined in step S8 that the second blood pump 6 has made the predetermined number of revolutions, the second blood pump 6 is stopped in step S9. Then, the process proceeds to step S10. If it is determined in step S8 that the second blood pump 6 has not made the predetermined number of revolutions yet, step S9 is skipped. Then, whether or not the first blood pump 5 and the second blood pump 6 each have made a predetermined number of revolutions is checked (step S10). If it is determined in step S10 that the first blood pump 5 and the second blood pump 6 each have not made the predetermined number of revolutions yet, the process returns to step S4. Then, the above series of control steps are performed again. If it is determined that the first blood pump 5 and the second blood pump 6 each have made the predetermined number of revolutions, the blood removal is ended. Thus, the whole process of blood removal is ended.

According to the second embodiment, during the blood removal, the control device 17 causes the first blood pump 5 to undergo normal rotation and the second blood pump 6 to undergo reverse rotation, whereby the priming solution in the blood circuit 1 is substituted with the blood of the patient, and the priming solution thus substituted is discharged from the blood circuit 1. Hence, in a configuration employing the single-needle double-pump method in which the only puncture needle 3 is connected to each of the distal ends of the arterial blood circuit 1a and the venous blood circuit 1b that are provided with the respective peristaltic pumps (the first blood pump 5 and the second blood pump 6), the priming solution having undergone the substitution can be automatically discharged from the blood circuit 1 during the blood removal.

The control device 17 according to the second embodiment activates the first blood pump 5 and the second blood pump 6 simultaneously at the time of blood removal. Therefore, the priming solution having undergone the substitution can be automatically discharged from the blood circuit 1 during the blood removal. Moreover, the blood removal can be finished in a shorter time. Furthermore, according to the second embodiment, the number of revolutions and the speed of rotation of each of the first blood pump 5 and the second blood pump 6 during the blood removal are set in accordance with the capacity of the portion between the site where the priming solution substituted with the blood is discharged (the site where the dialyzer-inlet-pressure chamber B2 is provided) and the site where a corresponding one of the first blood pump 5 and the second blood pump 6 is provided. Therefore, the priming solution having undergone the substitution can be discharged from the blood circuit 1 more smoothly and more correctly.

In particular, in the second embodiment, the overflow line L9 is provided between the first blood pump 5 and the second blood pump 6 in the blood circuit 1, and the control device 17 allows the priming solution substituted with the blood to be discharged through the overflow line L9 during the blood removal. Therefore, the priming solution can be smoothly discharged from the blood circuit 1 without using the blood purification membranes (the hollow fiber membranes (M) of the dialyzer 2) or the like.

Now a third embodiment of the present invention will be described.

A blood purification apparatus according to the third embodiment is a dialysis apparatus for giving a hemodialysis treatment, as in the first and second embodiments, and includes, as illustrated in FIG. 8, a blood circuit 1 including an arterial blood circuit 1a and a venous blood circuit 1b, a dialyzer 2 (a blood purification device) provided between the arterial blood circuit 1a and the venous blood circuit 1b and that purifies blood flowing in the blood circuit, a first blood pump 5 that is a peristaltic pump and is provided to the arterial blood circuit 1a, a second blood pump 6 that is a peristaltic pump and is provided to the venous blood circuit 1b, hematocrit sensors 7 and 8, a control device 17, and an ultrafiltration pump 13. Elements that are the same as those described in the first or second embodiments are denoted by corresponding ones of the reference numerals, and detailed description of those elements is omitted.

As in the first and second embodiments, during the blood removal, the control device 17 according to the third embodiment causes the first blood pump 5 to undergo normal rotation (the rotation in the direction a) and the second blood pump 6 to undergo reverse rotation (the rotation in the direction (b)), whereby the priming solution (the dialysate in the third embodiment, or a physiological saline solution) in the blood circuit 1 is substituted with the blood of the patient, and the priming solution thus substituted is discharged from the blood circuit 1.

More specifically, the control device 17 activates the first blood pump 5 and the second blood pump 6 simultaneously such that the first blood pump 5 undergoes normal rotation while the second blood pump 6 undergoes reverse rotation. Thus, the blood of the patient is introduced from the body of the patient into the blood circuit 1 through the puncture needle 3, and the priming solution is substituted with the blood. Furthermore, the ultrafiltration pump 13 is activated, whereby the priming solution thus substituted is discharged with the activation of the ultrafiltration pump.

In the third embodiment, to discharge the priming solution having undergone the substitution with the activation of the ultrafiltration pump 13, while the duplex pump 10 is activated, the atmosphere-releasing electromagnetic valve V9 is closed as illustrated in FIG. 8 (with the electromagnetic valves V4, V5, and V6 being open but with the electromagnetic valves V3 and V7 and the degassing electromagnetic valve V8 being closed), whereby the priming solution is allowed to flow through the dialysate drain line L2 after being filtered from the blood flow routes α into the dialysate flow routes β. Alternatively, for example, the duplex pump 10 may be stopped.

In the third embodiment, the number of revolutions and the speed of rotation of each of the first blood pump 5 and the second blood pump 6 during the blood removal are set in accordance with the capacity (the priming volume) of a portion between a site where the priming solution substituted with the blood is discharged (in the third embodiment, the site where the dialyzer 2 is provided) and a site where a corresponding one of the first blood pump 5 and the second blood pump 6 is provided. That is, the time of blood removal by the normal rotation of the first blood pump 5 and the time of blood removal by the reverse rotation of the second blood pump 6 can be made substantially equal, avoiding a situation where the blood removal by the second blood pump 6 is not complete even if the blood removal by the first blood pump 5 is complete or a situation where the blood removal by the first blood pump 5 is not complete even if the blood removal by the second blood pump 6 is complete.

In the third embodiment, the pressure generated when the priming solution substituted with the blood is filtered from the blood flow routes (α) into the dialysate flow routes (β) and is discharged is detectable by the pressure detection devices (P1 to P4). Furthermore, during the blood removal, the control device 17 controls the operation of the first blood pump 5 and the second blood pump 6 on the basis of the pressures detected by the pressure detection devices (P1 to P4). Therefore, if the pressure generated when the priming solution is filtered from the blood flow routes α into the dialysate flow routes (β) is increased during the blood removal, the number of revolutions and the speed of rotation of each of the first blood pump 5 and the second blood pump 6 are reduced, so that the occurrence of damage to the hollow fiber membranes (the filtering membranes) can be suppressed.

Now, a control process (a process of controlling the blood removal) performed by the control device 17 according to the third embodiment will be described with reference to the flow chart illustrated in FIG. 9. Note that, prior to the blood removal, the priming process is performed, and the blood circuit 1 is thus filled with the priming solution.

When the process of blood removal is started after the priming process, the ultrafiltration pump 13 is activated in step S1 and the first blood pump 5 is rotated in the normal direction (step S2) while the second blood pump 6 is rotated in the reverse direction (step S3). The speed of rotation of the ultrafiltration pump 13 is set such that the flow rate of the ultrafiltration pump 13 corresponds to the sum of the flow rates of the first blood pump 5 and the second blood pump 6.

Subsequently, whether or not the value detected by the pressure detection device P5 is at or below a warning point is checked in step S4. If it is determined that the value is at or below the warning point, the speed of rotation of the ultrafiltration pump 13 is reduced in step S5. Then, in step S6, whether or not either of the values detected by the pressure detection devices P2 and P3 is at or above a warning point is checked. If it is determined in step S4 that the value detected by the pressure detection device P5 is not at or below the warning point, step S5 is skipped and the process proceeds to step S6. If it is determined in step S6 that either of the values detected by the pressure detection devices P2 and P3 is at or above the warning point, the speeds of rotation of the first blood pump 5 and the second blood pump 6 are reduced in step S7. Then, in step S8, whether or not either of the values detected by the pressure detection devices P1 and P4 is at or below a warning point is checked. If it is determined in step S6 that neither of the values detected by the pressure detection devices P2 and P3 is at or above the warning point, step S7 is skipped and the process proceeds to step S8.

If it is determined in step S8 that neither of the values detected by the pressure detection devices P1 and P4 is at or below the warning point, the process proceeds to step S9, where whether or not the hematocrit sensors 7 and 8 have detected any blood within a predetermined period of time is checked. If no blood is detected, the process proceeds to step S10, where an alarm notifying a defect in blood removal is generated, and the blood removal is ended. If it is determined in step S6 that neither of the values detected by the pressure detection devices P2 and P3 is at or above the warning point, step S7 is skipped and the process proceeds to step S8. If it is determined in step S8 that either of the values detected by the pressure detection devices P1 and P4 is at or below the warning point, the process proceeds to step S10, where an alarm notifying a defect in blood removal is generated, and the blood removal is ended.

If the hematocrit sensors 7 and 8 have detected any blood within the predetermined period of time in step S9, whether or not the first blood pump 5 has made a predetermined number of revolutions (corresponding to the capacity (the priming volume) of the portion between the site where the priming solution substituted with the blood is discharged (in the third embodiment, the site where the dialyzer 2 is provided) and the site where the first blood pump 5 is provided) is checked (step S11). If it is determined that the first blood pump 5 has made the predetermined number of revolutions, the first blood pump 5 is stopped in step S12. Then, whether or not the second blood pump 6 has made a predetermined number of revolutions (corresponding to the capacity (the priming volume) of the portion between the site where the priming solution substituted with the blood is discharged (in the third embodiment, the site where the dialyzer 2 is provided) and the site where the second blood pump 6 is provided) is checked (step S13). If it is determined in step S11 that the first blood pump 5 has not made the predetermined number of revolutions yet, step S12 is skipped and the process proceeds to step S13.

If it is determined in step S13 that the second blood pump 6 has made the predetermined number of revolutions, the second blood pump 6 is stopped in step S14. Then, whether or not the first blood pump 5 and the second blood pump 6 each have made the predetermined number of revolutions is checked (step S15). If it is determined in step S15 that the first blood pump 5 and the second blood pump 6 each have made the predetermined number of revolutions, the blood removal is ended. If it is determined that the first blood pump 5 and the second blood pump 6 each have not made the predetermined number of revolutions yet, the process returns to step S4. Then, the above series of control steps are performed again.

According to the third embodiment, during the blood removal, the control device 17 causes the first blood pump 5 to undergo normal rotation and the second blood pump 6 to undergo reverse rotation, whereby the priming solution in the blood circuit 1 is substituted with the blood of the patient, and the priming solution thus substituted is discharged from the blood circuit 1. Therefore, in a configuration employing the single-needle double-pump method in which the only puncture needle 3 is connected to each of the distal ends of the arterial blood circuit 1a and the venous blood circuit 1b that are provided with the respective peristaltic pumps (the first blood pump 5 and the second blood pump 6), the priming solution having undergone the substitution can be automatically discharged from the blood circuit 1 during the blood removal.

The control device 17 according to the third embodiment activates the first blood pump 5 and the second blood pump 6 simultaneously at the time of blood removal. Therefore, the priming solution having undergone the substitution can be automatically discharged from the blood circuit 1 during the blood removal. Moreover, the blood removal can be finished in a shorter time. Furthermore, according to the third embodiment, the number of revolutions and the speed of rotation of each of the first blood pump 5 and the second blood pump 6 during the blood removal are set in accordance with the capacity of the portion between the site where the priming solution substituted with the blood is discharged (the site where the dialyzer 2 is provided) and the site where a corresponding one of the first blood pump 5 and the second blood pump 6 is provided. Therefore, the priming solution having undergone the substitution can be discharged from the blood circuit 1 more smoothly and more correctly.

According to the third embodiment, the dialyzer 2 (the blood purification device) includes the hollow fiber membranes M (the blood purification membranes) for purifying blood and that define the blood flow routes $\alpha$ in which the blood of the patient flows and the dialysate flow routes $\beta$ in which the dialysate flows. Furthermore, the control device 17 causes the priming solution substituted with the blood to be filtered from the blood flow routes ($\alpha$) into the dialysate flow routes ($\beta$) and is then discharged during the blood removal. Therefore, during the blood removal, the priming solution having undergone the substitution can be discharged automatically from the blood circuit 1 by using the blood purification membranes of the blood purification device (the hollow fiber membranes M of the dialyzer 2).

Furthermore, the blood purification apparatus includes the pressure detection devices (P1 to P4) capable of detecting the pressure generated when the priming solution substituted with the blood is discharged while being filtered from the blood flow routes ($\alpha$) into the dialysate flow routes ($\beta$). Furthermore, during the blood removal, the control device 17 controls the operation of the first blood pump 5 and the second blood pump 6 on the basis of the pressures detected by the pressure detection devices (P1 to P4). Therefore, the priming solution can be discharged from the blood circuit 1 in accordance with the filtering capability of the blood purification membranes (the hollow fiber membranes (M) of the dialyzer 2).

In particular, the blood purification apparatus according to the third embodiment includes the ultrafiltration pump 13 for removing water from the blood that is extracorporeally circulated through the blood circuit 1. Furthermore, at the time of blood removal, the control device 17 activates the ultrafiltration pump 13 and thus discharges the priming solution substituted with the blood. Therefore, during the blood removal, the priming solution having undergone the substitution can be discharged automatically from the blood circuit 1 by using the ultrafiltration pump 13.

While some embodiments have been described above, the present invention is not limited to such embodiments. For example, the site from which the priming solution having undergone the substitution is discharged from the blood circuit during the blood removal is not limited to the dialyzer 2 (in the first and third embodiments) or the overflow line L9 (in the second embodiment) and may be another site. Moreover, as long as the priming solution in the blood circuit 1 is substituted with the blood of the patient by rotating the first blood pump 5 in the normal direction and rotating the second blood pump 6 in the reverse direction during the blood removal, the first blood pump 5 and the second blood pump 6 may be activated alternately.

Furthermore, while the above embodiments each concerns a case where the blood purification device is the dialyzer 2 including the hollow fiber membranes (M), the blood purification device is not limited to the dialyzer 2 and may be a blood purification device of another mode that includes blood purification membranes different from the hollow fiber membranes (M). While the above embodiments are each applied to a dialysis apparatus used in hemodialysis treatment, the present invention may be applied to any other apparatus that is capable of purifying the blood of the patient while extracorporeally circulating the blood (for example, any of a blood purification apparatus, a blood-plasma-absorbing apparatus, and the like that are used in a hemodiafiltration method, a hemofiltration method, and AFBF).

The present invention is applicable to a blood purification apparatus of any other mode and intended for any other purposes, as long as the apparatus includes a control device that causes, during blood removal, a first blood pump to undergo normal rotation and a second blood pump to undergo reverse rotation so that a priming solution flowing in a blood circuit is substituted with the blood of a patient while the priming solution thus substituted is discharged from the blood circuit.

REFERENCE SIGN LIST 1 blood circuit
1a arterial blood circuit
1b venous blood circuit
2 dialyzer (blood purification device)
3 puncture needle (single needle)
4 wye
5 first blood pump
6 second blood pump
7, 8 hematocrit sensor
9 liquid-level-adjusting device
10 duplex pump
11, 12 filtration filter
13 ultrafiltration pump
14 pump
15 degassing chamber
16 collecting port
17 control device
L1 dialysate introduction line
L2 dialysate drain line
L9 overflow line
M hollow fiber membrane (blood purification membrane)
α blood flow route
β dialysate flow route

The invention claimed is:

1. A blood purification apparatus that performs blood purification treatment while extracorporeally circulating blood of a patient by using an only puncture needle, the apparatus comprising:
a blood circuit including an arterial blood circuit and a venous blood circuit to respective distal ends of which the only puncture needle is connectable, the blood circuit allowing the blood of the patient to be extracorporeally circulated from the distal end of the arterial blood circuit to the distal end of the venous blood circuit;
a blood purification device provided between the arterial blood circuit and the venous blood circuit and that purifies the blood of the patient flowing in the blood circuit;
a first blood pump that is a peristaltic pump provided to the arterial blood circuit and is capable of introducing the blood of the patient into the blood circuit through the puncture needle when activated to undergo normal rotation;
a second blood pump that is a peristaltic pump provided to the venous blood circuit and is capable of returning the blood in the blood circuit to the patient through the puncture needle when activated to undergo normal rotation; and
a control device that allows the blood of the patient to be extracorporeally circulated through the blood circuit by causing the first blood pump and the second blood pump to alternately undergo normal rotation,
wherein, during blood removal, the control device operates to substitute a priming solution in the blood circuit with the blood of the patient and the first blood pump undergoes normal rotation and the second blood pump undergoes reverse rotation to discharge the priming solution having undergone the substitution from the blood circuit.

2. The blood purification apparatus according to claim 1, wherein, when the blood removal is performed, the control device activates the first blood pump and the second blood pump simultaneously.

3. The blood purification apparatus according to claim 1, wherein a number of revolutions and a speed of rotation of each of the first blood pump and the second blood pump during the blood removal are set in accordance with a capacity of a portion between a site where the priming solution substituted with the blood is discharged and a site where a corresponding one of the first blood pump and the second blood pump is provided.

4. The blood purification apparatus according to claim 1, wherein the blood purification device includes blood purification membranes that purify the blood and define blood flow routes in which the blood of the patient flows and dialysate flow routes in which a dialysate flows, and wherein, during the blood removal, the control device causes the priming solution substituted with the blood to be discharged after being filtered from the blood flow routes into the dialysate flow routes.

5. The blood purification apparatus according to claim 4, further comprising a pressure detection device capable of detecting a pressure generated when the priming solution substituted with the blood is discharged while being filtered from the blood flow routes into the dialysate flow routes, wherein, during the blood removal, the control device controls the first blood pump and the second blood pump on basis of the pressure detected by the pressure detection device.

6. The blood purification apparatus according to claim 1, wherein the blood circuit includes an overflow line provided between the first blood pump and the second blood pump, and wherein, during the blood removal, the control device allows the priming solution substituted with the blood to be discharged through the overflow line.

7. The blood purification apparatus according to claim 4, further comprising an ultrafiltration pump for removing water from the blood that is extracorporeally circulated through the blood circuit, wherein, during the blood removal, the control device allows the priming solution substituted with the blood to be discharged by activating the ultrafiltration pump.

8. The blood purification apparatus according to claim 1, wherein the arterial blood circuit includes an air-bubble detection device.

9. The blood purification apparatus according to claim 8, wherein the arterial blood circuit includes an air-trap chamber upstream of the air-bubble detection device.

10. The blood purification apparatus according to claim 9, wherein the blood enters through the only puncture needle into the air-trap chamber of the arterial blood circuit before flowing into a dialyzer when the first blood pump rotates under normal rotation and the second blood pump is off.

11. The blood purification apparatus according to claim 1, wherein the venous blood circuit includes an air-bubble detection device.

12. The blood purification apparatus according to claim 11, wherein the venous blood circuit includes an air-trap chamber downstream of the air-bubble detection device.

13. The blood purification apparatus according to claim 12, wherein the blood passes through the air-trap chamber, then the air-bubble detection device, before passing through the only puncture needle when the second blood pump is operation in the normal rotation and the first blood pump stopped.

14. The blood purification apparatus according to claim 1, wherein the blood purification apparatus includes an overflow line that extends from a blood circuit to a dialysate flow route.

15. The blood purification apparatus according to claim 14, wherein the overflow line extends from a dialyzer-inlet-pressure chamber in the blood circuit to a dialysate drain line in the dialysate flow route.

16. The blood purification apparatus according to claim 15, wherein the overflow line includes an overflow clamp that opens and closes the overflow line.

17. The blood purification apparatus according to claim 1, wherein the blood circuit includes a wye with flexible tubes and the flexible tubes include a luer taper and screw that are connectable to a distal end of each of the arterial blood circuit and the venous blood circuit.

* * * * *